United States Patent [19]
Kansas

[11] Patent Number: 5,156,607
[45] Date of Patent: Oct. 20, 1992

[54] MANUAL SMALL INCISION CATARACT EXTRACTION METHOD AND INSTRUMENT

[75] Inventor: Peter G. Kansas, 101 Murray Ave., Delmar, N.Y. 12054

[73] Assignee: Peter G. Kansas, Albany, N.Y.

[21] Appl. No.: 765,533

[22] Filed: Sep. 25, 1991

[51] Int. Cl.$^5$ .................... A61F 9/00; A61F 2/16; A61B 17/32
[52] U.S. Cl. .................... 606/107; 606/167; 606/170; 623/6
[58] Field of Search .............. 606/107, 166, 167, 170, 606/172; 623/6

[56] References Cited

U.S. PATENT DOCUMENTS

| 2,521,161 | 9/1950 | Grover | 606/167 |
| 2,944,552 | 7/1960 | Cannon | 606/167 X |
| 4,251,887 | 2/1981 | Anis | 623/6 |
| 4,298,994 | 11/1981 | Clayman | 623/6 |
| 4,932,967 | 6/1990 | Kansas | 623/6 |
| 4,960,418 | 10/1990 | Tennant | 606/107 |

Primary Examiner—Ronald Frinks
Attorney, Agent, or Firm—Hayes & Reinsmith

[57] ABSTRACT

A microsurgical method and nucleotome for fragmentizing a cataractous endonucleus in a single cutting manuever is disclosed whereby the endonucleus is split into multiple fragments for quick and easy extraction.

20 Claims, 10 Drawing Sheets

MANUAL SMALL INCISION CATARACT EXTRACTION METHOD AND INSTRUMENT

FIELD OF THE INVENTION

This invention generally relates to a method and surgical instrument for use in the extraction of a cataractous endonucleus and specifically concerns a new and improved method and apparatus for trisecting that endonculeus in a single cutting movement thereby to split the endonucleus into three fragments for quick easy extraction.

BACKGROUND OF THE INVENTION

In recent years extracapsular cataract extraction, wherein at least a part of the capsular tissue is left intact within the eye, has overtaken intracapsular extraction involving the removal of the crystaline lens together with its supporting capsular tissue. In one of the techniquesphacoemulsification, one of the specialized techniques which is utilized in extracapsular cataract extraction, a portion of the anterior lens capsule is removed but the remainder of the capsule remains in the course of this technique wherein ultrasonic energy is used to break up the lens nucleus which is then aspirated.

The advantages of phacoemulsification include a small incision whereby mechanical vibration transforms lens matter into an emulsion which can be aspirated from the capsular bag and replaced by infusion fluid. However, there are disadvantages in that there is a higher incidence of complications due to the fact that this specialized technique is difficult, the lens material is more likely to become mixed with vetreous, and the iris may become damaged. In addition, many nuclei are just too dense for comfortable phacoemulsification. Moreover, the equipment is expensive.

Another of the techniques used in extracapsular cataract extraction provides for bisecting a cataractous nucleus of an eye with a knife-like instrument pressed against a so-called solid vectis or microcutting board positioned behind the nucleus and then extracting the bisected nuclear portions through an incision providing access to the anterior eye chamber. However, this technique places a premium on precision symmetry in the bisecting of the nucleus core so as to ensure nuclear fragments of common size to enable one to minimize the length of the required incision which, obviously, must be of sufficient size to accommodate removal of the largest sized fragment.

Another technique used by a number of ophthalmologists is an extracapsular extraction method wherein a limbal incision is extended for about 160° which permits the lens nucleus to be removed as a unit and the cortical material to be aspirated from the eye. With this type of extracapsular cataract extraction, the method is less complicated, for the technique is simpler than phacoemulsification, but the extensive wound requires longer time in healing, and longer convalescence and stabilization.

In each of these described methods, a "capsular bag" remains in place and becomes an ideal site for placement of intraocular lens (IOL) implant as fully described in my U.S. Pat. No. 4,932,967 dated Jun. 12, 1990 and entitled "Intraocular Lens Implant".

OBJECTS OF THE INVENTION

A primary aim of achieving simplicity in the surgical technique without postoperative complications and reduced possibilities of tissue irritation is continuously sought to ensure visual rehabilitation.

Accordingly, a primary object of this invention is to provide a new and improved microsurgical method of extracting a cataract which features a series of steps which require an incision of significantly reduced size coupled with ease in manually fragmentizing a cataractous endonucleus in a surgical technique involving significantly reduced trauma to an eye of a patient.

Another object of this invention is to provide a new and improved surgical instrument suited for manually cutting and removing a portion of a cataractous endonucleus of an eye and which effects synergistic results in quickly and easily dividing that nucleus core into multiple fragments in a single cutting maneuver while providing a passage for forceps for subsequent extraction of a remaining nuclear fragment upon removal of the instrument which occurs simultaneously with removal of an intermediate fragment of the nucleus core.

Yet another object of this invention is to provide such an instrument which is not only quick and easy to use, but features a design of remarkable simplicity adapted to be manufactured in a quick and easy manner at reasonable cost.

Other objects will be in part obvious and in part pointed out in detail hereinafter.

SUMMARY OF THE INVENTION

A microsurgical method of extracting a cataract performed in accordance with this invention comprises steps of making an incision to provide an opening to an anterior chamber of an eye, separating an inner cataractous endonucleus from softer surrounding ectonucleus layers, introducing through the incision and into the anterior chamber a solid vectis and a nucleotome having a cutting blade formed in a closed loop configuration, positioning the nucleotome and the vectis on opposite faces of the endonucleus, fragmentizing the endonucleus in one cutting maneuver by gently and slowly pressing the nucleotome and vectis together to cleanly split the endonucleus into at least three fragments, withdrawing the nucleotome and the vectis from the anterior chamber through the incision with an intermediate fragment of the endonucleus ensnared within the cutting blade of the nucleotome, and removing the remaining nuclear fragments from the anterior chamber of the eye.

In addition, a microsurgical instrument is provided by this invention particularly suited for cutting and removing a portion of a cataractous endonucleus of an eye in accordance with the above described method and comprises a handle with an attached blade having a knife-like cutting edge, the blade itself being formed in a closed loop configuration defining an opening for entrapping an intermediate portion of a cataractous endonucleus upon its being incised by the blade.

A better understanding of the objects, advantages, features, properties and relations of this invention will be obtained from the following detailed description and accompanying drawings which set forth an illustrative embodiment and is indicative of the way in which the principles of this invention are employed.

DETAILED DESCRIPTION OF A PREFERRED EMBODIMENT

Referring now in detail to the drawings, my invention specifically concerns extraction of a cataract from a human eye utilizing a new and improved microsurgical technique and instrument. As is known, a cataract is broadly defined as an opacity on or within the lens of an eye, and cataracts may be of a variety of different types which frequently result in the disorder having to be surgically extracted for improving one's vision, or for other medical or cosmetic reasons.

Figure 1:
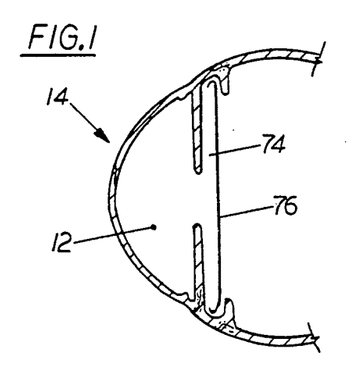
FIG. 1 is a cross-sectional schematic view of an eye with its normal lens removed.
Figure 2:
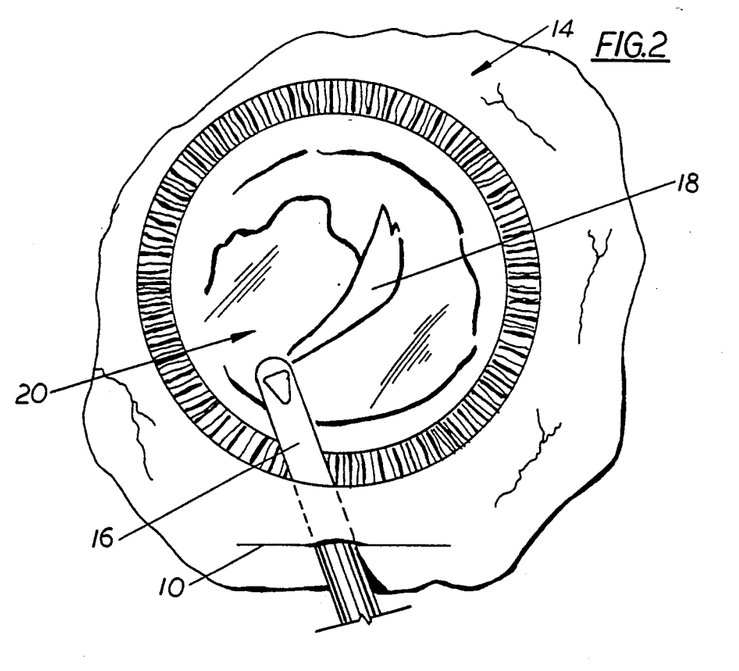
FIG. 2 is a front view, partly broken away, showing an anterior capsulotomy, being undertaken.

During extracapsular cataract extraction, the procedure according to my invention may be performed with a 4.0 to 4.5 mm incision 10 (FIG. 2), preferably one of a scleral pocket configuration, which is of significantly reduced size, made possible by my inventive technique and instrument as described below. Such an incision 10 provides access to an anterior chamber 12 of an eye 14 (FIG. 1) so as to then perform a conventional anterior capsulotomy, or excision of the anterior eye capsule 18, preferably by a well-known capsulorhexis technique utilizing a surgical instrument such as a cystotome 16 (FIG. 2). Whenever possible, it is preferred that the capsulorhexis technique be utilized, but it may have to be converted to (or combined with) a conventional so-called "can-opener" procedure.

Figure 3:
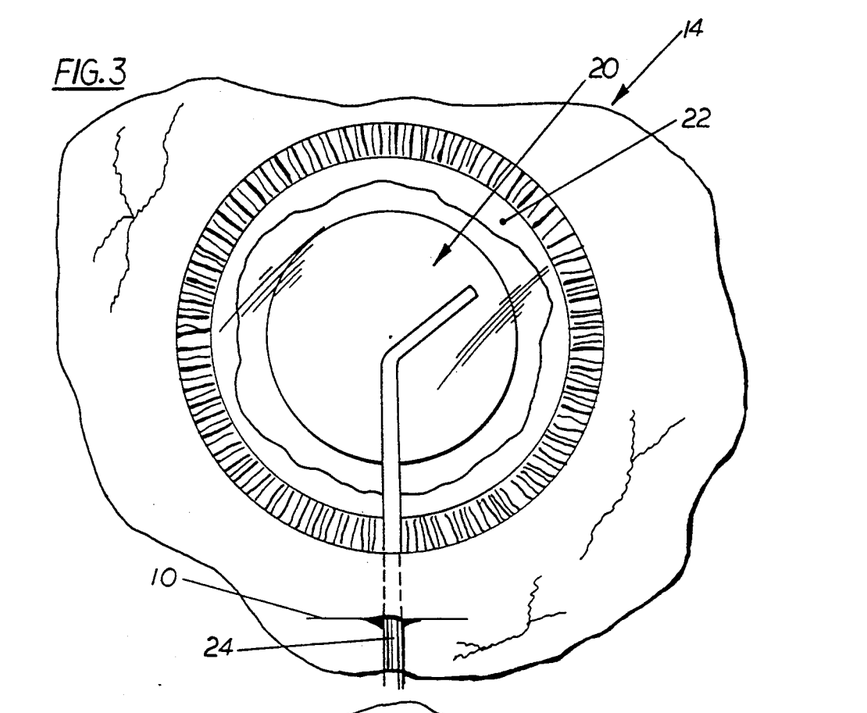
FIG. 3 is a front view, partly broken away, illustrating hydrodissection of an endonucleus core following the capsulotomy of FIG. 2.

Following the capsulotomy, a hard inner cataractous endonucleus or central core of the nucleus 20 of the cataract is delineated and separated from the softer outer nucleus layers 22 (ectonucleus) utilizing hydrodissection to reduce the mass for easier extraction. Hydrodissection involves use of a small cannula 24 (FIG. 3) and fluid such as a sterile saline solution which is injected into that nucleus 20 as deep as the tissue resistance allows to create a cleavage plane. This procedure delineates the nucleus core by repeated short bursts of irrigation. With younger patients, the nucleus core may become detached and prolapse so as to be conditioned for removal.

Figure 4:
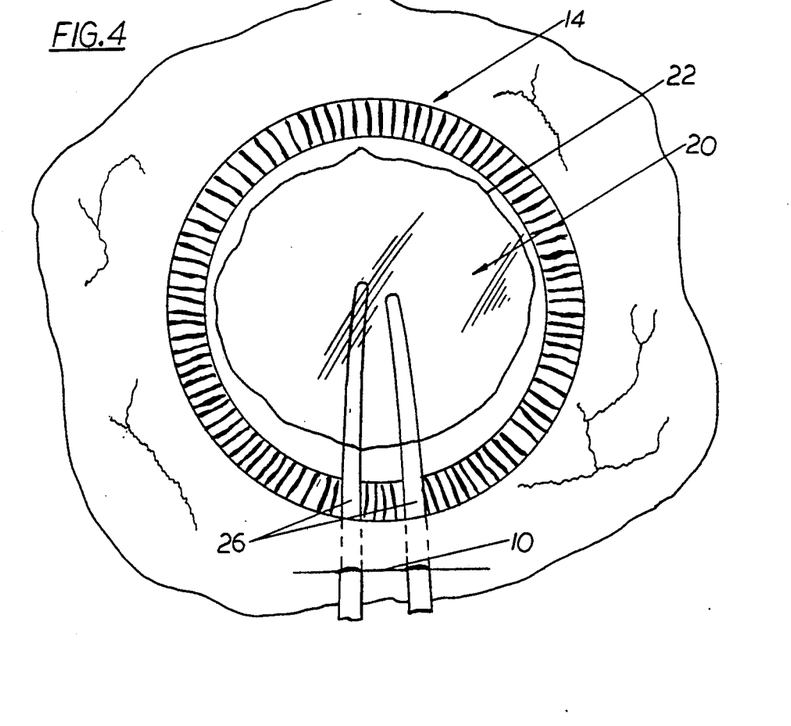
FIG. 4 is a front view, partly broken away, showing prolapsing of the endonucleus core.

Having created the smallest possible nuclear mass, the maximum possible room to operate within is then effected by prolapsing the delineated core 20 into the anterior chamber 12 (FIG. 4) wherein the core 20 will be in a position to be manually operated upon. This prolapsing step is preferably accomplished by bimanual manipulation of two modified Kuglen hooks 26 or similar instruments beginning at the superior pole of the core 20.

Figure 5:
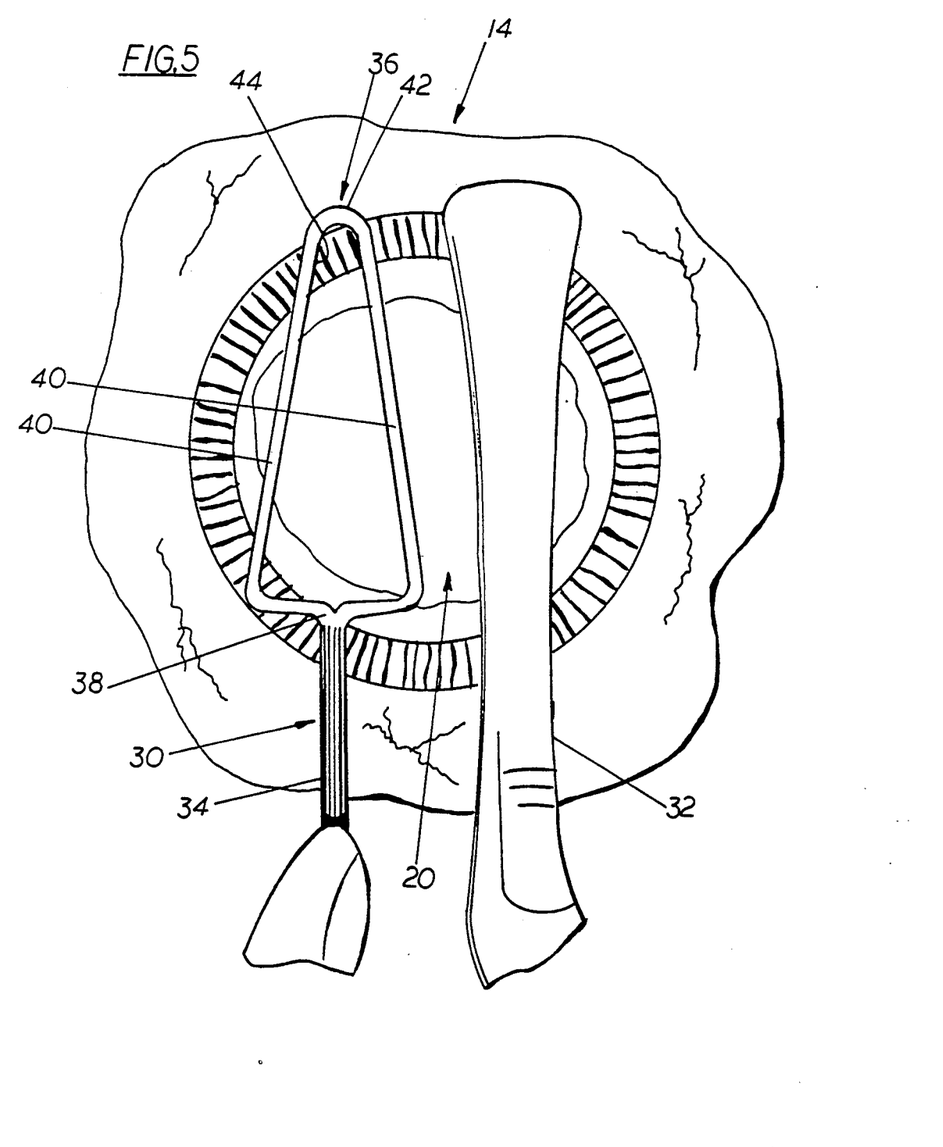
FIG. 5 is an enlarged front view, partly broken away, depicting the relative size of an eye structure in relation to certain instruments used in accordance with this invention.
Figure 6:
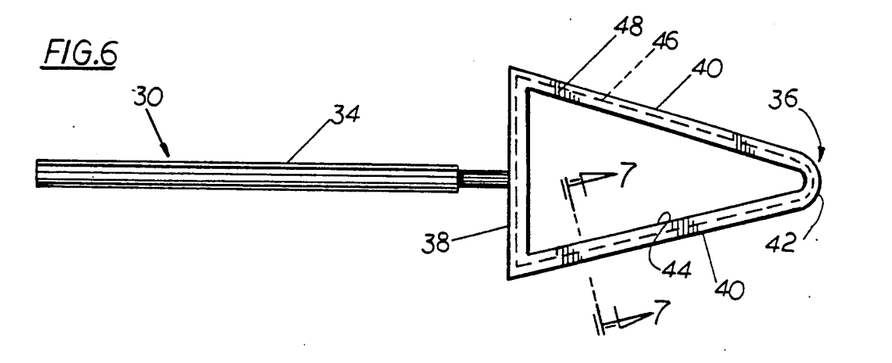
FIG. 6 is a plan view of a surgical instrument incorporating this invention.
Figure 17:
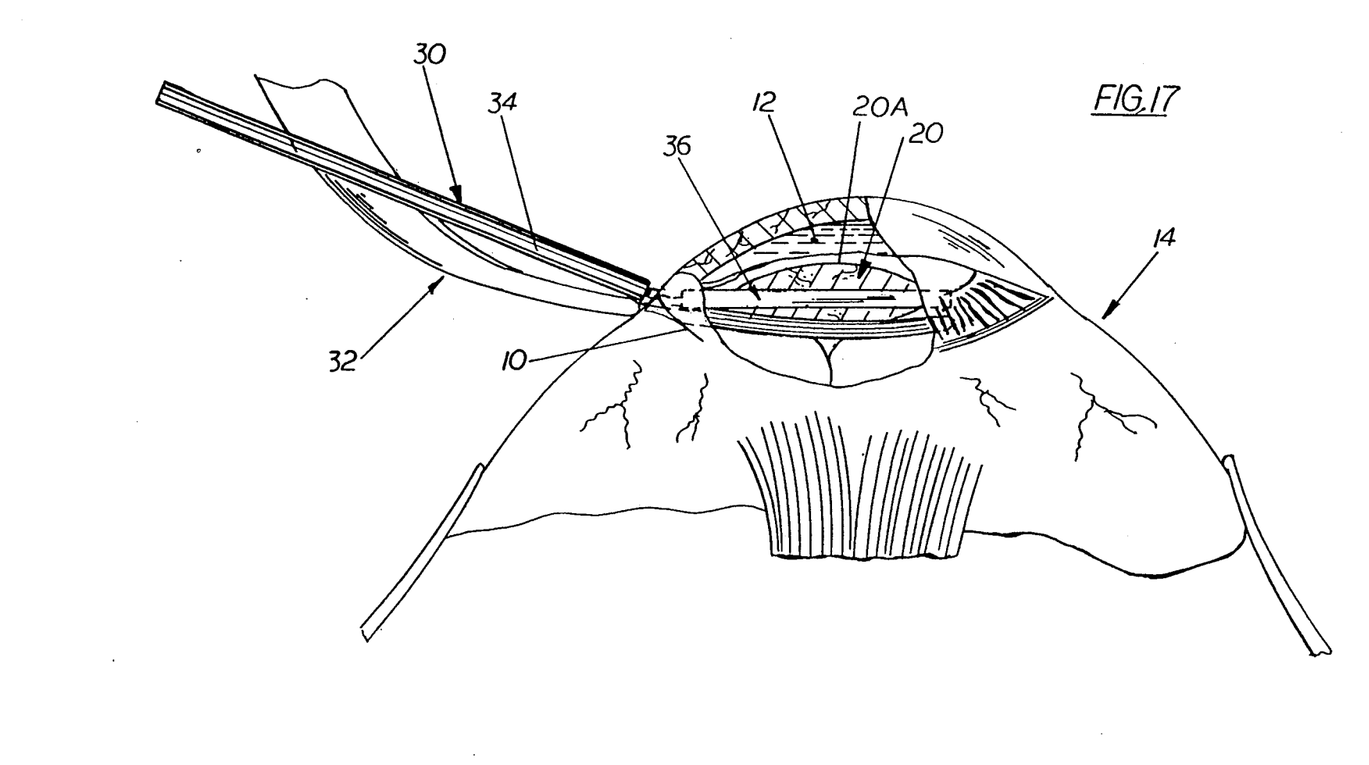
FIG. 17 is an enlarged cross-sectional schematic side view, partly broken away, showing an eye being fragmentized in accordance with the step of FIG. 10.

Then upon maximum viscoelastic anterior chamber stabilization, a unique nucleus phacofragmentation technique then is performed in accordance with this invention to manually fracture the nucleus core 20 of the cataract such that several small nuclear fragments are readily removed through the above described small incision 10. This invention utilizes a knife edged nucleotome 30 in cooperation with a solid vectis 32 which actually serves as a spatula-type microcutting board. The relative size of the eye structure in relation to these two instruments is depicted in FIG. 5 wherein it will be noted that the nucleotome 30 has a handle 34 (FIGS. 6, 8 and 17) which is connected to a cutting blade 36 featuring a unique closed loop configuration. The blade 36 is attached to a trailing base segment 38 which is interconnected by a pair of identical side segments 40 40 to a relatively short leading segment 42. By virtue of this construction, the cutting blade 36 of the nucleotome 30 comprises a plurality of interconnected longitudinally extending segments, preferably formed of a high grade surgical metal, which jointly define an opening 44 therein which, in this embodiment, has a truncated triangular configuration with the cutting edge 46 of blade 36 extending throughout its length about its entire periphery.

Figures 7, 8:
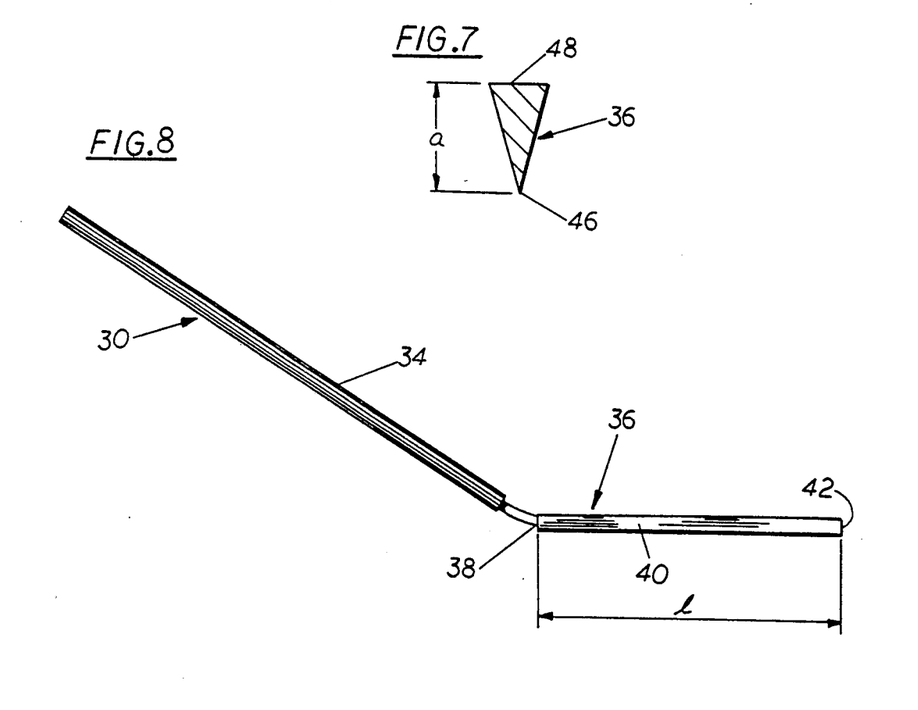
FIG. 7 is an enlarged cross-sectional view taken along line 7—7 of FIG. 6.
FIG. 8 is a side-elevational view of the instrument of FIG. 1.

More specifically, the nucleotome cutting blade may be about 0.4 to 0.5 mm in cross-sectional height (distance "a" in FIG. 7 from lower cutting edge 46 to upper face 48 of the blade 36) with an overall length "1" of about 9 mm (FIG. 8). The shorter leading segment 42 may be dimensioned to be about 1.5 to 2.0 mm in width with the relatively longer trailing base segment 38 having a maximum width of about 3.5 mm.

Figure 9:
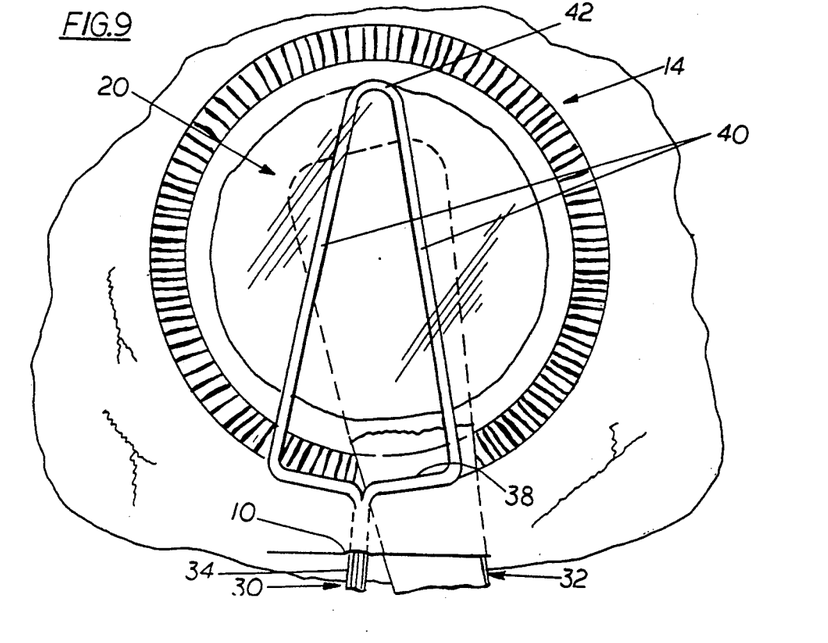
FIGS. 9 and 10 are front views, partly broken away, showing relative positioning of the instruments of FIG. 5 during a fragmentizing step performed in accordance with this invention.
Figure 10:
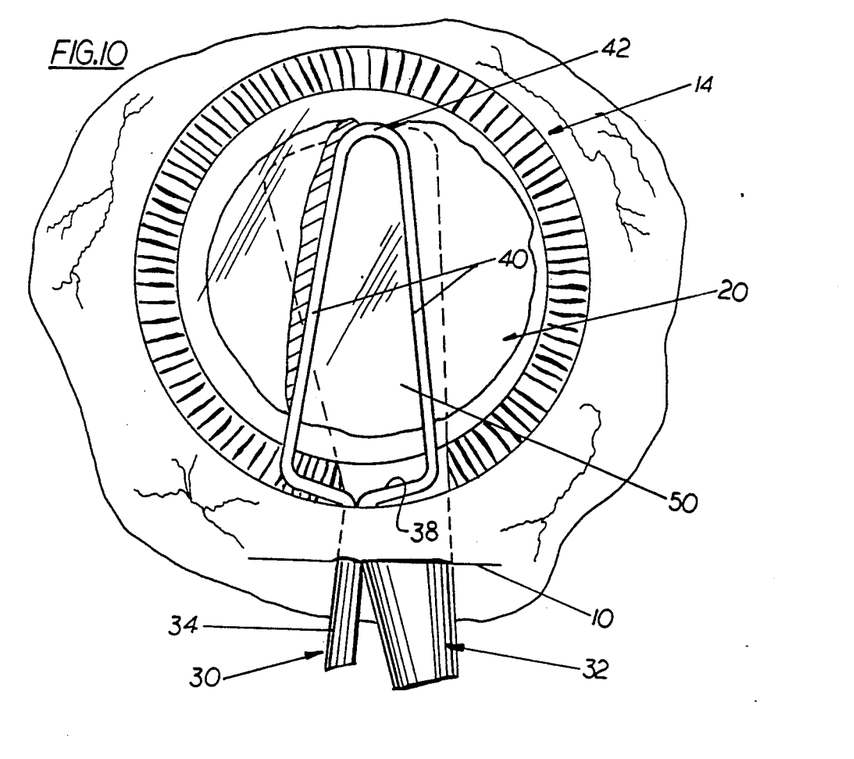
Figure 11:
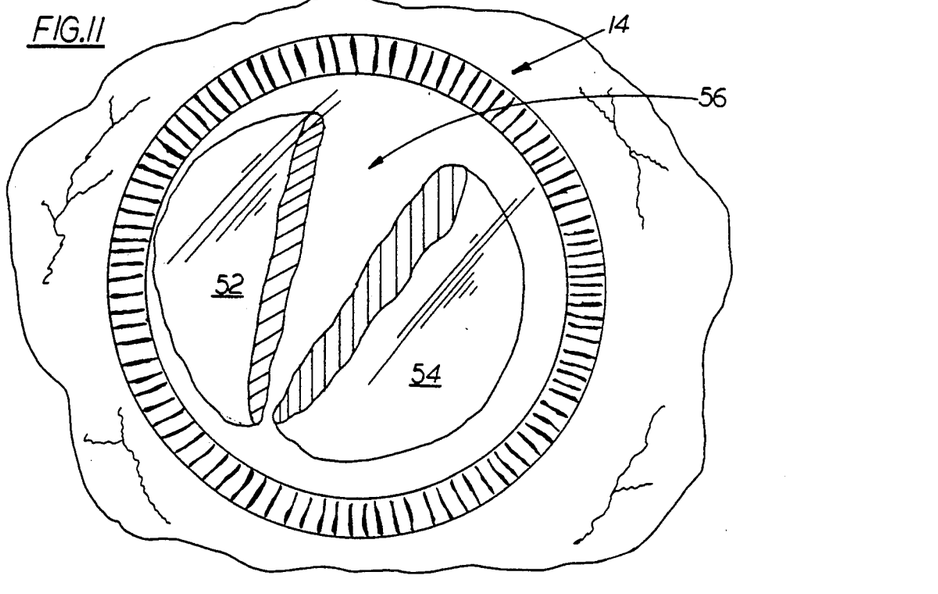
FIG. 11 is a front view illustrating remaining fragments of the endonucleus following removal of the instruments of FIG. 5 from the anterior chamber of the eye.
Figure 12:
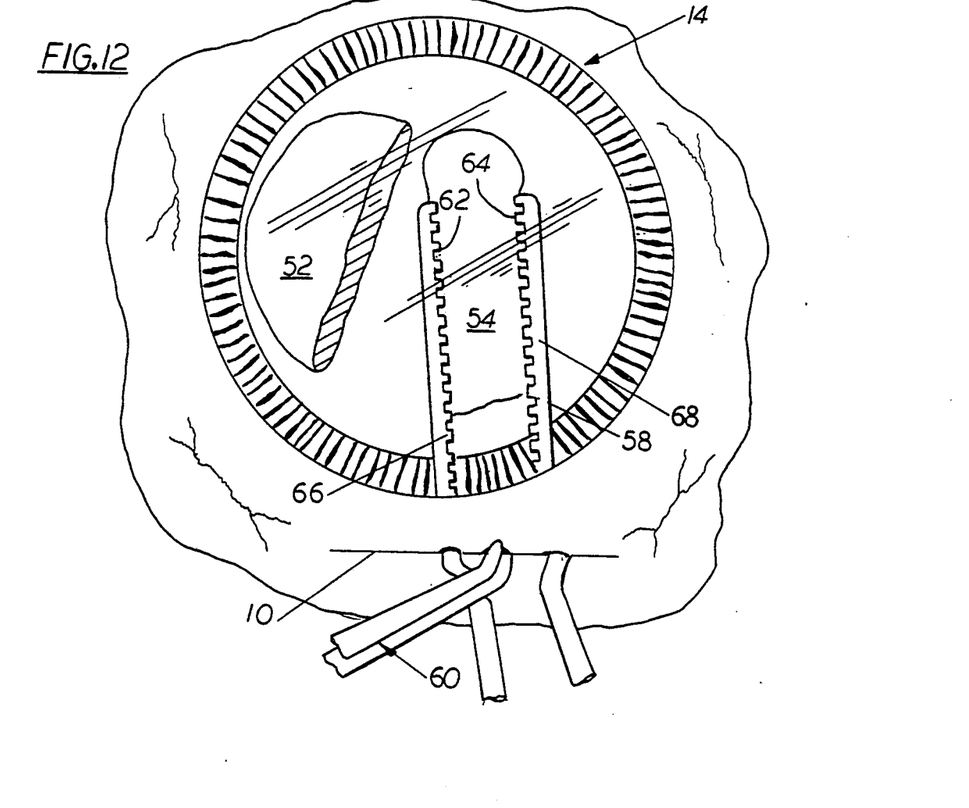
FIG. 12 is a front view, partly broken away, showing extraction of one of the remaining fragments from the anterior chamber of the eye.
Figure 13:
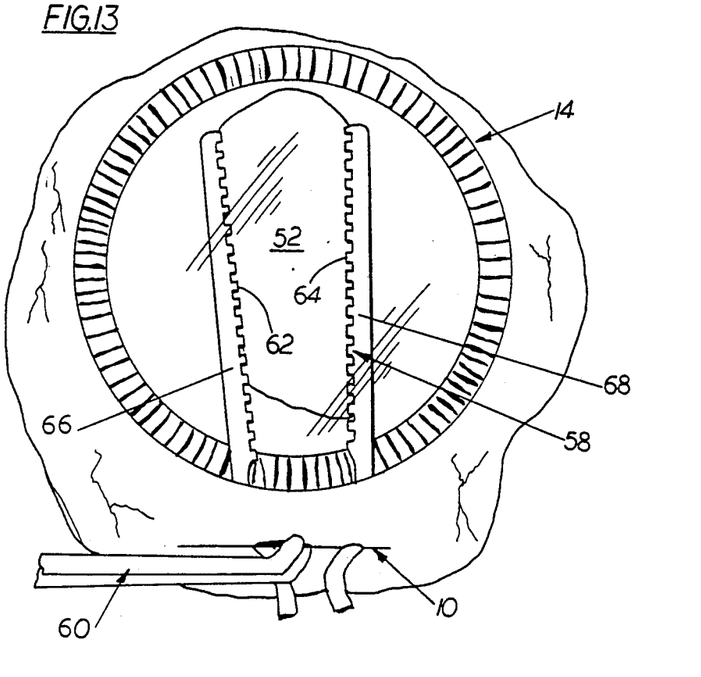
FIG. 13 is a front view, partly broken away, showing a remaining fragment within the anterior chamber of the eye prior to its extraction by forceps utilized in accordance with this invention.

Thus with the delineated nucleus core 20 prolapsed and manipulated into the anterior chamber 12 of the eye 14, the nucleotome 30 may be introduced first through incision 10 on top of the nucleus core 20, in centered relation thereto (FIG. 9), followed almost simultaneously by introduction of the vectis 32 behind or beneath the nucleus core 20 in underlying relation both to core 20 and to the nucleotome 30. Upon gently and slowly pressing the nucleotome 30 and vectis 32 (FIGS. 10 and 17) together, fragmentizing of the nucleus core 20 is effected to split it in unison into multiple fragments (FIG. 10), three fragments being shown in this embodiment. With the nucleotome 30 having been squarely centered on an anterior face 20A (FIG. 17) of the prolapsed nucleus core 20, intermediate fragment 50 is trapped within opening 44 within the confines of the closed loop of the nucleotome 30 during this trisecting maneuver and is thus readily adapted to be removed simultaneously with the withdrawal of the nucleotome 30 which preferably is withdrawn simultaneously with the vectis 32 through the incision 10. With the middle fragment 50 thus usually ensnared within the nucleotome 30 upon its removal from the anterior chamber 12, the remaining two fragments 52, 54 are then slightly separated by the described cutting maneuver of nucleotome 30 to automatically create a forceps passage 56 (FIG. 11) in preparation for a following extracting step to remove these remaining two fragments 52, 54. The anterior chamber 12 then is further stabilized, if necessary, by viscoelastic materials, and fragments 52, 54 are preferably extracted (FIGS. 12 and 13) upon being individually grasped by suitable special forceps 58 and carefully guided out of the anterior chamber 12 with the aid of a tweezer-like instrument 60 through incision 10. The smaller of fragments 52, 54 is extracted first if the fragments are asymmetrical. The forceps 58 preferably used are those illustrated (FIGS. 12 and 13) using two parallel rows of blunted teeth such as at 62, 64 on 9 mm jaws 66, 68 for quick and easy maneuvering of the fragments 52, 54 into a most favorable position for extraction through incision 10.

Figure 14:
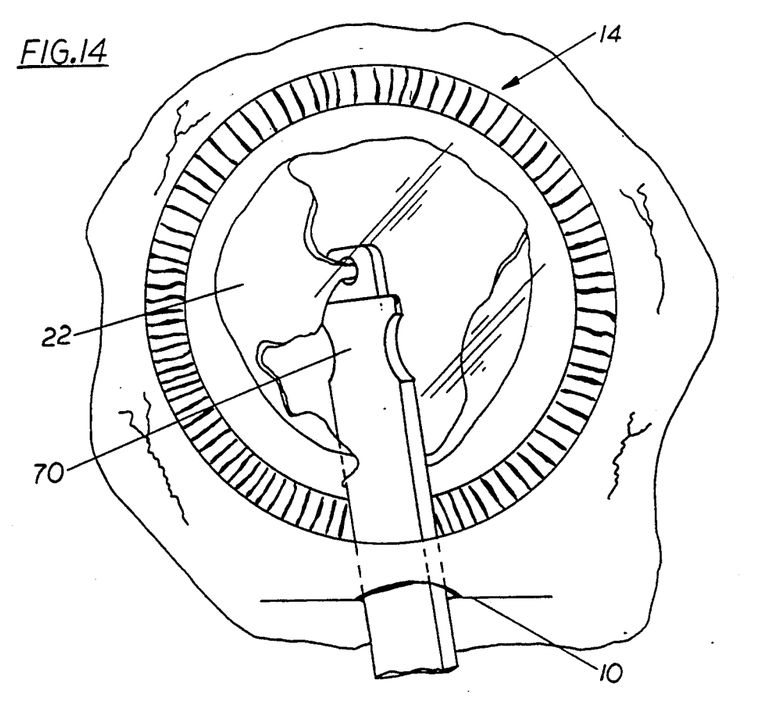
FIG. 14 is a front view, partly broken away, showing an epinucleus aspiration step.
Figure 15:
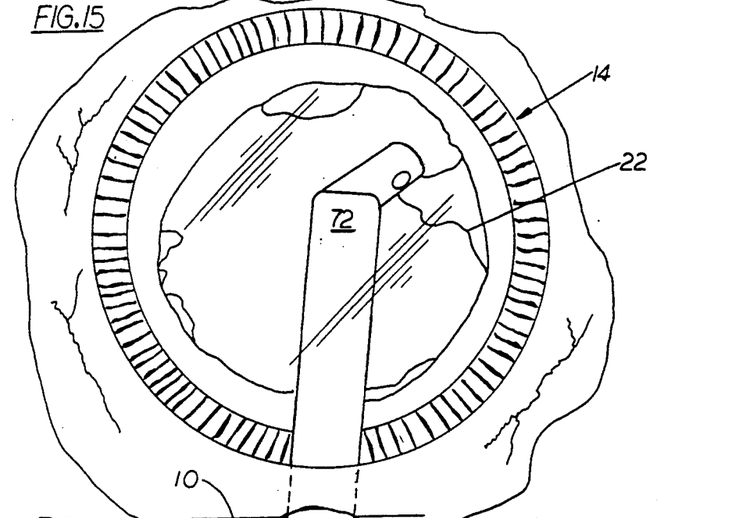
FIG. 15 is a front view, partly broken away, showing a cortex aspiration step.

Cortical clean-up may then be carried out using conventional irrigation-aspiration cannulae or the like in a conventional way to aspirate remaining ectonucleus and viscoelastic sludge. Frequently this step can be significantly facilitated with additional hydrodissection of the remaining ectonucleus layer 22 from the underlying cortex into the center of the pupil. This step may be accomplished with use of a 0.5 mm coaxial cannula tip 70 used in a conventional manner (FIG. 14). Cortex removal is completed by switching (FIG. 15) to a 0.3 mm coaxial handpiece 72 used in a well known manner to effect required peripheral engagement and central stripping.

Figure 16:
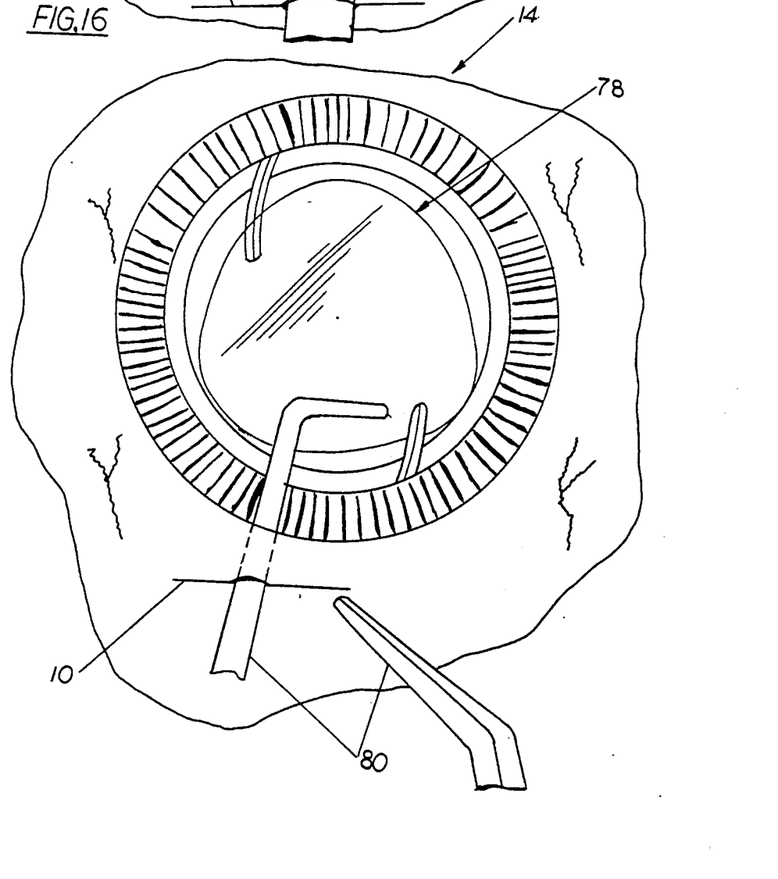
FIG. 16 is a front view, partly broken away, showing an IOL insertion and placement of an IOL.

Following cortical clean-up, a lens (IOL) placement within the posterior chamber 74 of the lens capsule or sac 76 (FIG. 1) may now be effected (FIG. 16). Such a technique and an accepted IOL such as at 78 are aided in insertion and placement by suitable instruments 80. The IOL 78 is fully described in my above referenced U.S. Pat. No. 4,932,967, the teachings of which are incorporated herein by reference. The so-called "in-the-bag" IOL placement takes full advantage of capsulorhexis capsulotomy, and the reduced incision requirements of the disclosed nucleotome 30 permit use of implants of reduced size.

The wound is then closed, preferably by suturing the scleral pocket incision 10 with two absorbably polyglycotic 8-0 sutures which produce a watertight closure and after absorption should leave no suture-induced astigmatism.

This invention also contemplates use of a vibratory driver of known construction coupled to the nucleotome for selected applications.

Figure 18A:
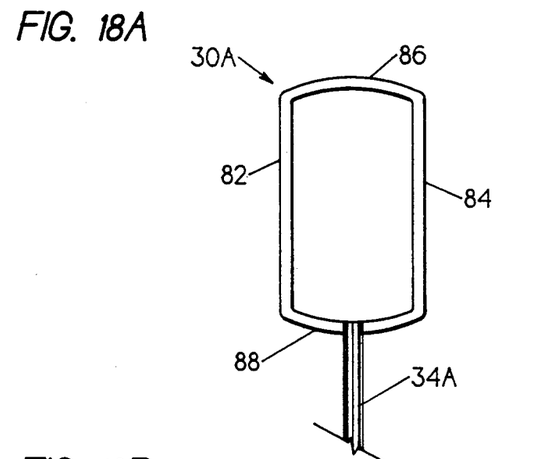
FIGS. 18A, 18B and 18C are plan views, partly broken away, showing different embodiments of surgical instruments incorporating this invention.
Figure 18B:
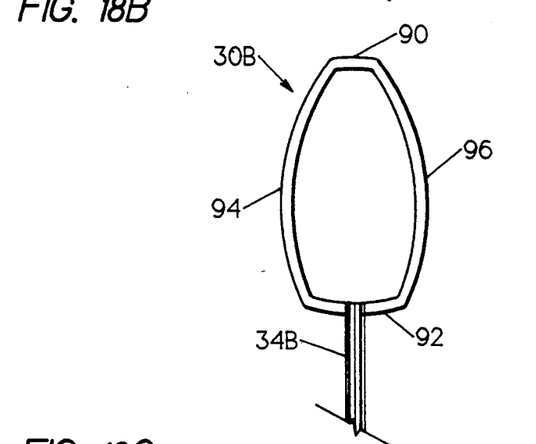
Figure 18C:
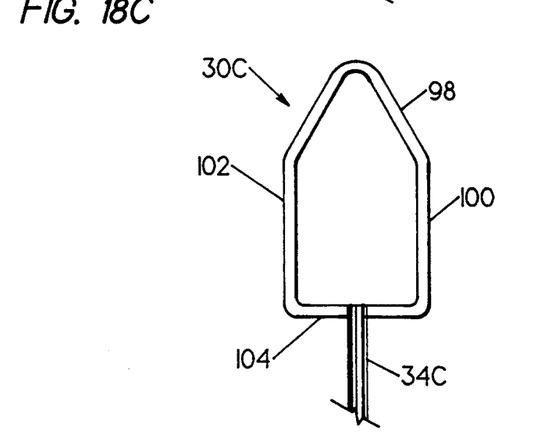

In addition, the blade of the nucleotome may be different from that shown in the first described embodiment. As illustrated in FIGS. 18A, 18B and 18C, each of the nucleotome blades 30A, 30B and 30C are of a closed loop configuration which will be understood to provide a cutting edge extending throughout the entire length of the loop about its periphery for splitting and entrapping a portion of a cataractous nucleus within the closed loop of the blade upon the nucleus being incised by the blade.

More specifically, blade 30A (FIG. 18A) includes parallel straight sides 82, 84 interconnected by arcuate leading and trailing segments 86, 88, trailing segment 88 being connected to handle 34A. Blade 30B (FIG. 18B) also has arcuate leading and trailing segments 90, 92 which in this embodiment are interconnected by arcuate side segments 94, 96 of identical construction in mirror-image relation to one another and connected through trailing segment 92 to handle 34B. Blade 30C (FIG. 18C) has a v-shaped leading segment 98 with straight side segments 100, 102 connected by a rectilinear trailing segment 104 to handle 34C. Each of the blades 30A, 30B and 30C will be understood to be formed of high grade surgical metal and to have a triangular cross-section of generally common size defining a surgical cutting edge for trisecting the cataractous nucleus.

As will be apparent to persons skilled in the art, various modifications, adaptations and variations of the forgoing specific disclosure can be made without departing from the teachings of this invention.

I claim:

1. A method of performing cataract microsurgery comprising the steps of
    making an incision to provide an opening to an anterior chamber of an eye;
    separating an inner cataractous endonucleus from softer surrounding endonucleus layers;
    introducing into the anterior chamber through the incision a solid vectis and a nucleotome having a cutting blade with a closed loop configuration;
    positioning the nucleotome and the vectis adjacent opposite faces of the endonucleus;
    fragmentizing the endonucleus in one cutting maneuver to split the endonucleus into three fragments;
    withdrawing the nucleotome and an intermediate fragment of the endonucleus in unison through the incision from the anterior chamber,
    extracting the vectis through the incision from the anterior chamber; and
    manually removing the two remaining fragments of the endonucleus by forceps, after the withdrawing and extracting steps, through the incision from the anterior chamber of the eye.

2. The method of claim 1 wherein the withdrawing and extracting steps include removing the nucleotome, the intermediate fragment of the endonucleus, and the vectis simultaneously from the anterior chamber.

3. The method of claim 1 wherein the positioning step includes positioning the nucleotome on an anterior face of the endonucleus and positioning the solid vectis behind the endonucleus prior to the fragmentizing step.

4. The method of claim 1 wherein the fragmentizing step includes manually pressing the nucleotome and vectis together to split the endonucleus.

5. The method of claim 1 including the step of stabilizing the anterior chamber by introducing viscoelastic materials into the anterior chamber of the eye after the separating step.

6. The method of claim 1 wherein the separating step includes the steps of performing a capsulotomy and then delineating the endonucleus by hydrodissection.

7. The method of claim 1 including the step of prolapsing the cataractous endonucleus into the anterior chamber of the eye after the separating step.

8. The method of claim 1 including the step of irrigating the anterior chamber with viscoelastic materials after the incision is made to effect hydrodissection of the ectonucleus layers from the underlying cortex to facilitate the separating step.

9. The method of claim 1 including the step of irrigating the anterior chamber with viscoelastic materials prior to the fragmentizing and removing steps.

10. The method of claim 9 including the further step of aspirating the anterior chamber to remove the ectonucleus and viscoelastic sludge remaining after the removing step.

11. The method of claim 10 including the step of inserting and placing an intraocular lens implant in the posterior chamber of the eye after the irrigating step.

12. The method of claim 11 including the step of closing the incision to provide a watertight closure after the inserting and placing step.

13. A surgical instrument for cutting and removing a portion of a cataractous nucleus of an eye and comprising
a handle, and a blade attached to the handle, the blade being of a multiple segment construction formed in a closed loop configuration including a pair of relatively longer, identical side segments in mirror-image relation to one another, and the blade having a knife-like surgical cutting edge formed along a base of the blade segments to extend about the entire periphery of the loop for splitting a cataractous nucleus and entrapping a portion thereof within the closed loop of the blade upon the nucleus being incised by the blade.

14. The instrument of claim 13 wherein the blade includes a plurality of elongated segments each having a triangular cross-section of generally common size throughout its length defining a knife-like surgical cutting edge for trisecting the cataractous nucleus.

15. The instrument of claim 13 wherein the closed loop configuration of the blade defines an opening of truncated triangular configuration.

16. The instrument of claim 13 wherein the cutting blade is formed of high grade surgical metal.

17. A surgical instrument for cutting and removing a portion of a cataractous nucleus of an eye and comprising
a handle, and a blade attached to the handle, the blade having a cutting edge, and the blade being formed in a closed loop configuration with the cutting edge extending throughout its length about the entire periphery of the loop for splitting a cataractous nucleus and entrapping a portion thereof within the closed loop of the blade upon the nucleus being incised by the blade, the closed loop configuration of the cutting blade being formed by generally straight leading and trailing segments, and a pair of generally straight side segments each interconnecting corresponding ends of the leading and trailing segments.

18. The instrument of claim 17 wherein the cutting blade closed loop configuration defines an opening of truncated triangular configuration.

19. A surgical instrument for cutting and removing a portion of a cataractous nucleus of an eye and comprising
a handle, and a blade attached to the handle, the blade having a cutting edge, and the blade being formed in a closed loop configuration with the cutting edge extending throughout its length about the entire periphery of the loop for splitting a cataractous nucleus and entrapping a portion thereof within the closed loop of the blade upon the nucleus being incised by the blade,
the cutting blade comprising a plurality of interconnected longitudinally extending segments formed of metal and having a common sized triangular cross-section defining a knife-like surgical cutting edge, the interconnected segments including a relatively short leading segment, a pair of relatively longer side segments identical to one another and a trailing segment, the side segments connecting corresponding ends of the leading and trailing segments, the trailing segment of the blade being connected to the handle.

20. The instrument of claim 19 wherein the interconnected segments of the cutting blade jointly define an opening therein having a truncated triangular configuration.

* * * * *